United States Patent [19]

Loewe et al.

[11] 4,069,325

[45] Jan. 17, 1978

[54] 3-CARBALKOXYAMINO-1H-2,1,4-BENZO-THIADIAZINE DERIVATIVES

[75] Inventors: Heinz Loewe, Kelkheim, Taunus; Josef Urbanietz, Schwalbach, Taunus; Dieter Duwel, Hofheim, Taunus; Reinhard Kirsch, Niederjosbach, Taunus, all of Germany

[73] Assignee: Hoechst Aktiengesellschaft, Frankfurt (Main), Germany

[21] Appl. No.: 724,246

[22] Filed: Sept. 17, 1976

[30] Foreign Application Priority Data

Sept. 19, 1975 Germany .............................. 2541742

[51] Int. Cl.$^2$ .................. C07D 285/16; A61K 31/54

[52] U.S. Cl. ...................................... 424/246; 544/11; 260/575; 560/13

[58] Field of Search ...................... 260/243 R; 424/246

[56] References Cited

U.S. PATENT DOCUMENTS

| 3,655,657 | 4/1972 | Adams | 260/243 |
|---|---|---|---|
| 3,796,710 | 3/1974 | Barker et al. | 260/243 |

*Primary Examiner*—John M. Ford
*Attorney, Agent, or Firm*—Curtis, Morris & Safford

[57] ABSTRACT

3-Carbalkoxyamino-1H-2,1,4-benzothiadiazine derivatives are disclosed as well as a process for their manufacture. The compounds are suitable for combatting helminths and especially gastrointestinal Strongylides and liver flukes.

7 Claims, No Drawings

3-CARBALKOXYAMINO-1H-2,1,4-BENZO-THIADIAZINE DERIVATIVES

The present invention relates to 3-carbalkoxyamino-1H-2,1,4-benzothiadiazine derivatives and to a process for preparing them.

The present invention provides anthelmintically active 3-carbalkoxyamino-1H-2,1,4-benzothiadiazine derivatives of the formula (1)

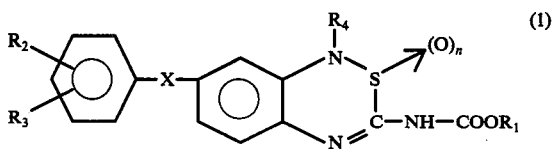
(1)

in which $R_1$ represents alkyl having from 1 to 4 carbon atoms, $R_2$ and $R_3$ each represent, independently from each other, a hydrogen atom, alkoxy having from 1 to 4 carbon atoms, halogen, trifluoromethyl, alkyl having from 1 to 4 carbon atoms or cyano, $R_4$ stands for hydrogen, an acyl radical having from 2 to 4 carbon atoms or a benzoyl radical, $n$ represents the FIGS. 0 or 1, and X stands for the groups —O—$SO_2$— or —$SO_2$—O—.

As alkyl radicals in the substituents $R_1$, $R_2$ and $R_3$ there may be mentioned: Methyl, etyl, propyl, isopropyl, butyl, secondary butyl, tertiary butyl. As alkoxy groups in the substituents $R_2$ and $R_3$ there may be mentioned: Methoxy, ethoxy, propoxy, isopropxy and butoxy. As halogen atoms in the substituents $R_2$ and $R_3$ there may be mentioned: Fluorine, chlorine, bromine and iodine.

Preference is given in particular to those compounds of the formula (1), in which $R_1$ stands for methyl, ethyl, propyl or butyl, $R_2$ is hydrogen and $R_3$ is hydrogen, chlorine, bromine, trifluoromethyl, methyl, ethyl, methoxy or ethoxy, $R_3$ preferably standing in the 3-position of the phenyl ring.

The invention further provides
a. a process for the preparation of 1H-2,1,4-benzothiadiazine derivatives of the formula (1), in which $R_1$, $R_2$ and $R_3$ and X are defined as in formula (1) above, and $n$ stands for 0, and in which $R_4$ represents hydrogen, which comprises reducing an o-nitro-phenyl-thionocarbamoyl-carbaminate of the formula (2)

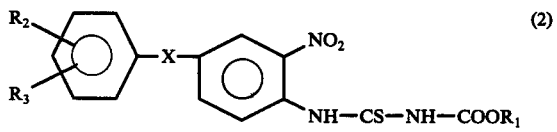
(2)

in which $R_1$, $R_2$ and $R_3$ and X are defined as above, with an alkali metal dithionite in an alkaline solution;

b. a process for the preparation of 1H-2,1,4-benzothiadiazine derivatives of the formula (1), in which $R_1$, $R_2$ and $R_3$ and X are defined as above and $n$ stands for 0, and in which $R_4$ stands for an acyl radical having from 2 to 4 carbon atoms or for a benzoyl radical, which comprises reacting a 2,1,4-benzothiadiazine derivative of the formula (1), in which $R_1$, $R_2$ and $R_3$ are defined as above and $n$ stands for 0, and in which $R_4$ represents hydrogen, with an acid halide, particularly an acid chloride, or with an acid anhydride which are derived from an aliphatic carboxylic acid having from 2 to 4 carbon atoms or from benzoic acid, preferably in the presence of a base;

c. a process for the preparation of 1H-2,1,4-benzothiadiazine derivatives of the formula (1), in which $R_1$, $R_2$ and $R_3$ as well as X are defined as above and $n$ stands for 1, and in which $R_4$ represents hydrogen, which comprises oxidizing a 2,1,4-benzothiadiazine of the formula (1), in which $R_1$, $R_2$ and $R_3$ and X are defined as above and $n$ stands for 0, and in which $R_4$ represents hydrogen, with a peroxo acid.

The process mentioned under a) above is suitably carried out in a way that an o-nitro-phenyl-thionocarbamoyl-carbaminate of the formula (2) is dissolved in an aqueous solution of a base, such as sodium hydroxide or potassium hydroxide, and is mixed in the atmosphere of an inert gas, such as nitrogen, with a reducing agent, in particular a dithionite, such as sodium dithionite, which is suitably dissolved in water, at a temperature in the range of from 10° to 50° C, depending on the reactivity of the starting compound used. After the reaction has been completed, the product is acidified with a mineral acid, such as hydrochloric acid, or a sufficiently strong organic acid, such as acetic acid, and the separated precipitate is isolated by filtration.

As o-nitro-phenyl-thionocarbamoyl-carbaminates of the formula (2) used for carrying out the process according to a) above, the following compounds may be mentioned, for example:

2-Nitro-4-phenoxysulfonyl-phenyl-thionocarbamoyl-methylcarbaminate,
2-nitro-4-(4-chloro-phenoxysulfonyl)-phenyl-thionocarbamoyl-methylcarbaminate.
2-nitro-4-(3-chloro-phenoxysulfonyl)-phenyl-thionocarbamoyl-methylcarbaminate,
2-nitro-4-(2-chloro-phenoxysulfonyl)-phenyl-thionocarbamoyl-methylcarbaminate,
2-nitro-4-(2,5-dichloro-phenoxysulfonyl)-phenyl-thionocarbamoyl-methylcarbaminate,
2-nitro-4-(3,5-dichloro-phenoxysulfonyl)-phenyl-thionocarbamoyl-methylcarbaminate,
2-nitro-4-(4-bromo-dichloro-phenoxysulfonyl)-phenyl-thionocarbamoyl-methylcarbaminate,
2-nitro-4-(3-bromo-dichloro-phenoxysulfonyl)-phenyl-thionocarbamoyl-methylcarbaminate,
2-nitro-4-(2-bromo-dichloro-phenoxysulfonyl)-phenyl-thionocarbamoyl-methylcarbaminate,
2-nitro-4-(4-methyl-dichloro-phenoxysulfonyl)-phenyl-thionocarbamoyl-methylcarbaminate,
2-nitro-4-(3-methyl-dichloro-phenoxysulfonyl)-phenyl-thionocarbamoyl-methylcarbaminate,
2-nitro-4-(2-methyl-dichloro-phenoxysulfonyl)-phenyl-thionocarbamoyl-methylcarbaminate,
2-nitro-4-(4-t.butyl-dichloro-phenoxysulfonyl)-phenyl-thionocarbamoyl-methylcarbaminate,
2-nitro-4-(2,4-dimethyl-dichloro-phenoxysulfonyl)-phenyl-thionocarbamoyl-methylcarbaminate,
2-nitro-4-(2-chloro-4-methyl-phenoxysulfonyl)-phenyl-thionocarbamoyl-methylcarbaminate,
2-nitro-4-(2-chloro-6-methyl-phenoxysulfonyl)-phenyl-thionocarbamoyl-methylcarbaminate,
2-nitro-4-(3-chloro-4-methyl-phenoxysulfonyl)-phenyl-thionocarbamoyl-methylcarbaminate,
2-nitro-4-(3-chloro-6-methyl-phenoxysulfonyl)-phenyl-thionocarbamoyl-methylcarbaminate,
2-nitro-4-(4-chloro-2-methyl-phenoxysulfonyl)-phenyl-thionocarbamoyl-methylcarbaminate, 2-nitro-4-(4-chloro-3-methyl-phenoxysulfonyl)-phenyl-thionocarbamoyl-methylcarbaminate,
2-nitro-4-(3-trifluoromethyl-phenoxysulfonyl)-phenyl-thionocarbamoyl-methylcarbaminate,
2-nitro-4-(4-methoxy-phenoxysulfonyl)-phenyl-thionocarbamoyl-methylcarbaminate,
2-nitro-4-(3-methoxy-phenoxysulfonyl)-phenyl-thionocarbamoyl-methylcarbaminate,
2-nitro-4-(2-methoxy-phenoxysulfonyl)-phenyl-thionocarbamoyl-methylcarbaminate,
2-nitro-4-(4-propoxy-phenoxysulfonyl)-phenyl-thionocarbamoyl-methylcarbaminate,
2-nitro-4-(4-isopropoxy-phenoxysulfonyl)-phenyl-thionocarbamoyl-methylcarbaminate,
2-nitro-4-(4-butoxy-phenoxysulfonyl)-phenyl-thionocarbamoyl-methylcarbaminate,
2-nitro-4-(4-isobutoxy-phenoxysulfonyl)-phenyl-thionocarbamoyl-methylcarbaminate,
2-nitro-4-(3-cyano-phenoxysulfonyl)-phenyl-thionocarbamoyl-methylcarbaminate,
2-nitro-4-phenoxysulfonyl-phenyl-thionocarbamoyl-ethylcarbaminate,
2-nitro-4-phenoxysulfonyl-phenyl-thionocarbamoyl-propylcarbaminate,
2-nitro-4-phenoxysulfonyl-phenyl-thionocarbamoyl-isopropylcarbaminate,
2-nitro-4-phenoxysulfonyl-phenyl-thionocarbamoyl-butylcarbaminate,
2-nitro-4-phenoxysulfonyl-phenyl-thionocarbamoyl-isobutylcarbaminate,
2-nitro-4-phenoxysulfonyl-phenyl-thionocarbamoyl-tert.butylcarbaminate,
2-nitro-4-phenylsulfonyloxy-phenyl-thionocarbamoyl-methylcarbaminate,
2-nitro-4-(4-chloro-phenylsulfonyloxy)-phenyl-thionocarbamoyl-methylcarbaminate,
2-nitro-4-(3-chloro-phenylsulfonyloxy)-phenyl-thionocarbamoyl-methylcarbaminate,
2-nitro-4-(2-chloro-phenylsulfonyloxy)-phenyl-thionocarbamoyl-methylcarbaminate,
2-nitro-4-(2,5-dichloro-phenylsulfonyloxy)-phenyl-thionocarbamoyl-methylcarbaminate,
2-nitro-4-(3,4-dichloro-phenylsulfonyloxy)-phenyl-thionocarbamoyl-methylcarbaminate,
2-nitro-4-(3,5-dichloro-phenylsulfonyloxy)-phenyl-thionocarbamoyl-methylcarbaminate,
2-nitro-4-(4-bromo-phenylsulfonyloxy)-phenyl-thionocarbamoyl-methylcarbaminate,
2-nitro-4-(3-bromo-phenylsulfonyloxy)-phenyl-thionocarbamoyl-methylcarbaminate,
2-nitro-4-(2-bromo-phenylsulfonyloxy)-phenyl-thionocarbamoyl-methylcarbaminate,
2-nitro-4-(4-methyl-phenylsulfonyloxy)-phenyl-thionocarbamoyl-methylcarbaminate,
2-nitro-4-(3-methyl-phenylsulfonyloxy)-phenyl-thionocarbamoyl-methylcarbaminate,
2-nitro-4-(2-methyl-phenylsulfonyloxy)-phenyl-thionocarbamoyl-methylcarbaminate,
2-nitro-4-(4-tert.butyl-phenylsulfonyloxy)-phenyl-thionocarbamoyl-methylcarbaminate,
2-nitro-4-(2-chloro-4-methyl-phenylsulfonyloxy)-phenyl-thionocarbamoyl-methylcarbaminate,
2-nitro-4-(2-chloro-6-methyl-phenylsulfonyloxy)-phenyl-thionocarbamoyl-methylcarbaminate,
2-nitro-4-(3-chloro-4-methyl-phenylsulfonyloxy)-phenyl-thionocarbamoyl-methylcarbaminate,
2-nitro-4-(3-chloro-6-methyl-phenylsulfonyloxy)-phenyl-thionocarbamoyl-methylcarbaminate,
2-nitro-4-(4-chloro-2-methyl-phenylsulfonyloxy)-phenyl-thionocarbamoyl-methylcarbaminate,
2-nitro-4-(4-chloro-3-methyl-phenylsulfonyloxy)-phenyl-thionocarbamoyl-methylcarbaminate,
2-nitro-4-(3-trifluoromethyl-phenylsulfonyloxy)-phenyl-thionocarbamoyl-methylcarbaminate,
2-nitro-4-(4-methoxy-phenylsulfonyloxy)-phenyl-thionocarbamoyl-methylcarbaminate,
2-nitro-4-(3-methoxy-phenylsulfonyloxy)-phenyl-thionocarbamoyl-methylcarbaminate,
2-nitro-4-(2-methoxy-phenylsulfonyloxy)-phenyl-thionocarbamoyl-methylcarbaminate,
2-nitro-4-(4-propoxy-phenylsulfonyloxy)-phenyl-thionocarbamoyl-methylcarbaminate,
2-nitro-4-(2-isopropoxy-phenylsulfonyloxy)-phenyl-thionocarbamoyl-methylcarbaminate,
2-nitro-4-(4-butoxy-phenylsulfonyloxy)-phenyl-thionocarbamoyl-methylcarbaminate,
2-nitro-4-(4-isobutoxy-phenylsulfonyloxy)-phenyl-thionocarbamoyl-methylcarbaminate,
2-nitro-4-phenylsulfonyloxy-phenyl-thionocarbamoyl-ethylcarbaminate,
2-nitro-4-phenylsulfonyloxy-phenyl-thionocarbamoyl-propylcarbaminate,
2-nitro-4-phenylsulfonyloxy-phenyl-thionocarbamoyl-isopropylcarbaminate,
2-nitro-4-phenylsulfonyloxy-phenyl-thionocarbamoyl-butylcarbaminate,
2-nitro-4-phenylsulfonyloxy-phenyl-thionocarbamoyl-isobutylcarbaminate,
2-nitro-4-phenylsulfonyloxy-phenyl-thionocarbamoyl-tert.butylcarbaminate,
2-nitro-4-(3-trifluoromethyl-phenylsulfonyloxy)-phenyl-thionocarbamoyl-ethylcarbaminate,
2-nitro-4-(3-trifluoromethyl-phenylsulfonyloxy)-phenyl-thionocarbamoyl-isopropylcarbaminate,
2-nitro-4-(3-trifluoromethyl-phenylsulfonyloxy)-phenyl-thionocarbamoyl-isobutylcarbaminate.

According to the process described under a) above, the following 2,1,4-benzothiadiazine derivatives of the formula (1) are obtained, for example, from the compounds mentioned before:

3-Carbomethoxyamino-7-(1H-2,1,4-benzothiadiazine)-sulfonic acid-phenylester,
3-carbomethoxyamino-7-(1H-2,1,4-benzothiadiazine)-sulfonic acid-4-chlorophenylester,
3-carbomethoxyamino-7-(1H-2,1,4-benzothiadiazine)-sulfonic acid-3-chlorophenylester,
3-carbomethoxyamino-7-(1H-2,1,4-benzothiadiazine)-sulfonic acid-2-chlorophenylester,
3-carbomethoxyamino-7-(1H-2,1,4-benzothiadiazine)-sulfonic acid-2,5-dichlorophenylester,
3-carbomethoxyamino-7-(1H-2,1,4-benzothiadiazine)-sulfonic acid-3,5-dichloro-phenylester,
3-carbomethoxyamino-7-(1H-2,1,4-benzothiadiazine)-sulfonic acid-4-bromophenylester,
3-carbomethoxyamino-7-(1H-2,1,4-benzothiadiazine)-sulfonic acid-3-bromophenylester,
3-carbomethoxyamino-7-(1H-2,1,4-benzothiadiazine)-sulfonic acid-2-bromophenylester,
3-carbomethoxyamino-7-(1H-2,1,4-benzothiadiazine)-sulfonic acid-4-methylphenylester,
3-carbomethoxyamino-7-(1H-2,1,4-benzothiadiazine)-sulfonic acid-3-methylphenylester,
3-carbomethoxyamino-7-(1H-2,1,4-benzothiadiazine)-sulfonic acid-2-methylphenylester, 3-carbomethoxyamino-7-(1H-2,1,4-benzothiadiazine)-sulfonic acid-4-t.butylphenylester,
3-carbomethoxyamino-7-(1H-2,1,4-benzothiadiazine)-sulfonic acid-2,4-dimethylphenylester,
3-carbomethoxyamino-7-(1H-2,1,4-benzothiadiazine)-sulfonic acid-2-chloro-4-methyl-phenylester,
3-carbomethoxyamino-7-(1H-2,1,4-benzothiadiazine)-sulfonic acid-2-chloro-6-methyl-phenylester,
3-carbomethoxyamino-7-(1H-2,1,4-benzothiadiazine)-sulfonic acid-3-chloro-4-methyl-phenylester,
3-carbomethoxyamino-7-(1H-2,1,4-benzothiadiazine)-sulfonic acid-3-chloro-6-methyl-phenylester,
3-carbomethoxyamino-7-(1H-2,1,4-benzothiadiazine)-sulfonic acid-4-chloro-2-methyl-phenylester,
3-carbomethoxyamino-7-(1H-2,1,4-benzothiadiazine)-sulfonic acid-4-chloro-3-methyl-phenylester,
3-carbomethoxyamino-7-(1H-2,1,4-benzothiadiazine)-sulfonic acid-3-trifluoro-methyl-phenylester,
3-carbomethoxyamino-7-(1H-2,1,4-benzothiadiazine)-sulfonic acid-4-methoxy-phenylester,
3-carbomethoxyamino-7-(1H-2,1,4-benzothiadiazine)-sulfonic acid-3-methoxy-phenylester,
3-carbomethoxyamino-7-(1H-2,1,4-benzothiadiazine)-sulfonic acid-2-methoxy-phenylester,
3-carbomethoxyamino-7-(1H-2,1,4-benzothiadiazine)-sulfonic acid-4-propoxy-phenylester,
3-carbomethoxyamino-7-(1H-2,1,4-benzothiadiazine)-sulfonic acid-4-isopropoxy-phenylester,
3-carbomethoxyamino-7-(1H-2,1,4-benzothiadiazine)-sulfonic acid-4-butoxy-phenylester,
3-carbomethoxyamino-7-(1H-2,1,4-benzothiadiazine)-sulfonic acid-4-isobutoxy-phenylester,
3-carbethoxyamino-7-(1H-2,1,4-benzothiadiazine)-sulfonic acid-phenylester,
3-carbopropoxyamino-7-(1H-2,1,4-benzothiadiazine)-sulfonic acid-phenylester,
3-isopropoxycarbonylamino-7-(1H-2,1,4-benzothiadiazine)-sulfonic acid-phenylester,
3-carbobutoxyamino-7-(1H-2,1,4-benzothiadiazine)-sulfonic acid-phenylester,
3-isobutoxycarbonylamino-7-(1H-2,1,4-benzothiadiazine)-sulfonic acid-phenylester,
3-carbo-t.butoxyamino-7-(1H-2,1,4-benzothiadiazine)-sulfonic acid-phenylester,
3-carbomethoxyamino-7-phenylsulfonyloxy-1H-2,1,4-benzothiadiazine,
3-carbomethoxyamino-7-(4-chloro-phenylsulfonyloxy)-1H-2,1,4-benzothiadiazine,
3-carbomethoxyamino-7-(3-chloro-phenylsulfonyloxy)-1H-2,1,4-benzothiadiazine,
3-carbomethoxyamino-7-(2-chloro-phenylsulfonyloxy)-1H-2,1,4-benzothiadiazine,
3-carbomethoxyamino-7-(2,5-dichloro-phenylsulfonyloxy)-1H-2,1,4-benzothiadiazine,
3-carbomethoxyamino-7-(3,4-dichloro-phenylsulfonyloxy)-1H-2,1,4-benzothiadiazine,
3-carbomethoxyamino-7-(3,5-dichloro-phenylsulfonyloxy)-1H-2,1,4-benzothiadiazine,
3-carbomethoxyamino-7-(4-bromo-phenylsulfonyloxy)-1H-2,1,4-benzothiadiazine,
3-carbomethoxyamino-7-(3-bromo-phenylsulfonyloxy)-1H, 2,1,4-benzothiadiazine,
3-carbomethoxyamino-7-(2-bromo-phenylsulfonyloxy)-1H-2,1,4-benzothiadiazine,
3-carbomethoxyamino-7-(4-methyl-phenylsulfonyloxy)-1H-2,1,4-benzothiadiazine,
3-carbomethoxyamino-7-(3-methyl-phenylsulfonyloxy)-1H-2,1,4-benzothiadiazine,
3-carbomethoxyamino-7-(2-methyl-phenylsulfonyloxy)-1H-2,1,4-benzothiadiazine,
3-carbomethoxyamino-7-(4-tert.butyl-phenylsulfonyloxy)-1H-2,1,4-benzothiadiazine,
3-carbomethoxyamino-7-(2-chloro-4-methyl-phenylsulfonyloxy)-1H-2,1,4-benzothiadiazine,
3-carbomethoxyamino-7-(2-chloro-6-methyl-phenylsulfonyloxy)-1H-2,1,4-benzothiadiazine,
3-carbomethoxyamino-7-(3-chloro-4-methyl-phenylsulfonyloxy)-1H-2,1,4-benzothiadiazine,
3-carbomethoxyamino-7-(3-chloro-6-methyl-phenylsulfonyloxy)-1H-2,1,4-benzothiadiazine,
3-carbomethoxyamino-7-(4-chloro-2-methyl-phenylsulfonyloxy)-1H-2,1,4-benzothiadiazine,
3-carbomethoxyamino-7-(4-chloro-3-methyl-phenylsulfonyloxy)-1H-2,1,4-benzothiadiazine,
3-carbomethoxyamino-7-(3-trifluoromethyl-phenylsulfonyloxy)-1H-2,1,4-benzothiadiazine,
3-carbomethoxyamino-7-(4-methoxy-phenylsulfonyloxy)-1H-2,1,4-benzothiadiazine,
3-carbomethoxyamino-7-(3-methoxy-phenylsulfonyloxy)-1H-2,1,4-benzothiadiazine,
3-carbomethoxyamino-7-(2-methoxy-phenylsulfonyloxy)-1H-2,1,4-benzothiadiazine,
2-carbomethoxyamino-7-(4-propoxy-phenylsulfonyloxy)-1H-2,1,4-benzothiadiazine,
3-carbomethoxyamino-7-(4-isopropoxy-phenylsulfonyloxy)-1H-2,1,4-benzothiadiazine,
3-carbomethoxyamino-7-(4-butoxy-phenylsulfonyloxy)-1H-2,1,4-benzothiadiazine,
3-carbomethoxyamino-7-(4-isobutoxy-phenylsulfonyloxy)-1H-2,1,4-benzothiadiazine,
3-carbethoxyamino-7-phenylsulfonyloxy-1H-2,1,4-benzothiadiazine,
3-carbopropoxyamino-7-phenylsulfonyloxy-1H-2,1,4-benzothiadiazine,
3-isopropoxycarbonylamino-7-phenylsulfonyloxy-1H-2,1,4-benzothiadiazine,
3-carbobutoxyamino-7-phenylsulfonyloxy-1H-2,1,4-benzothiadiazine,
3-isobutoxycarbonylamino-7-phenylsulfonyloxy-1H-2,1,4-benzothiadiazine,
3-carbo-t.butoxyamino-7-phenylsulfonyloxy-1H-2,1,4-benzothiadiazine,
3-carbethoxyamino-7-(3-trifluoromethyl-phenylsulfonyloxy)-1H-2,1,4-benzothiadiazine,
3-isopropoxycarbonylamino-7-(3-trifluoromethyl-phenylsulfonyloxy)-1H-2,1,4-benzothiadiazine,
3-isobutoxycarbonylamino-7-(3-trifluoromethyl-phenylsulfonyloxy)-1H-2,1,4-benzothiadiazine.

The process described under (b) above is suitably carried out in a way that a solution of the corresponding 1H-2,1,4-benzothiadiazine derivative of the formula (1), in which $R_4$ represents hydrogen, is mixed with a reactive acid derivative in a solvent which is able to bind the hydrogen chloride formed in the reaction with acid chloride and/or the acid set free in the reaction with anhydride, such as pyridine and its homologues or quinoline, and is reacted with said acid derivative, depending on its reactivity, for 1 to 10 hours at a temperature in the range of from −20° C to +30° C.

As reactive acid derivatives there are mentioned in particular acid chlorides, such as acetyl chloride, propionyl chloride, benzoyl chloride, or acid anhydrides, such as acetic acid anhydride or propionic acid anhydride.

In order to isolate the reaction product, the reaction mixture is suitably diluted with water, and by shaking with an inert solvent that is not miscible with water, the reaction product is transferred into the organic layer, from which it may be obtained by evaporation of the solvent. Suitable solvents of this kind are, for example, acetic ester, diethylether, diisopropylether, methylene chloride, chloroform, benzene, and other substances. As starting compounds for the process described under (b) above there are mentioned the following 1H-2,1,4-benzothiadiazines of the formula (1):

3-Carbomethoxyamino-7-(1H-2,1,4-benzothiadiazine)-sulfonic acid-phenylester,
3-carbomethoxyamino-7-(1H-2,1,4-benzothiadiazine)-sulfonic acid-4-chloro-phenylester,
3-carbomethoxyamino-7-(1H-2,1,4-benzothiadiazine)-sulfonic acid-3-chloro-phenylester,
3-carbomethoxyamino-7-(1H-2,1,4-benzothiadiazine)-sulfonic acid-2-chloro-phenylester,
3-carbomethoxyamino-7-(1H-2,1,4-benzothiadiazine)-sulfonic acid-2,5-dichloro-phenylester,
3-carbomethoxyamino-7-(1H-2,1,4-benzothiadiazine)-sulfonic acid-3,5-dichloro-phenylester,
3-carbomethoxyamino-7-(1H-2,1,4-benzothiadiazine)-sulfonic acid-4-bromo-phenylester,
3-carbomethoxyamino-7-(1H-2,1,4-benzothiadiazine)-sulfonic acid-3-bromo-phenylester,
3-carbomethoxyamino-7-(1H-2,1,4-benzothiadiazine)-sulfonic acid-2-bromo-phenylester,
3-carbomethoxyamino-7-(1H-2,1,4-benzothiadiazine)-sulfonic acid-4-methyl-phenylester,
3-carbomethoxyamino-7-(1H-2,1,4-benzothiadiazine)-sulfonic acid-3-methyl-phenylester,
3-carbomethoxyamino-7-(1H-2,1,4-benzothiadiazine)-sulfonic acid-2-methyl-phenylester,
3-carbomethoxyamino-7-(1H-2,1,4-benzothiadiazine)-sulfonic acid-4-t.butyl-phenylester,
3-carbomethoxyamino-7-(1H-2,1,4-benzothiadiazine)-sulfonic acid-2,4-dimethyl-phenylester,
3-carbomethoxyamino-7-(1H-2,1,4-benzothiadiazine)-sulfonic acid-2-chloro-4-methyl-phenylester,
3-carbomethoxyamino-7-(1H-2,1,4-benzothiadiazine)-sulfonic acid-2-chloro-6-methyl-phenylester,
3-carbomethoxyamino-7-(1H-2,1,4-benzothiadiazine)-sulfonic acid-3-chloro-4-methyl-phenylester,
3-carbomethoxyamino-7-(1H-2,1,4-benzothiadiazine)-sulfonic acid-3-chloro-6-methyl-phenylester,
3-carbomethoxyamino-7-(1H-2,1,4-benzothiadiazine)-sulfonic acid-4-chloro-2-methyl-phenylester,
3-carbomethoxyamino-7-(1H-2,1,4-benzothiadiazine)-sulfonic acid-4-chloro-3-methyl-phenylester,
3-carbomethoxyamino-7-(1H-2,1,4-benzothiadiazine)-sulfonic acid-3-trifluoromethyl-phenylester,
3-carbomethoxyamino-7-(1H-2,1,4-benzothiadiazine)-sulfonic acid-4-methoxy-phenylester,
3-carbomethoxyamino-7-(1H-2,1,4-benzothiadiazine)-sulfonic acid-3-methoxy-phenylester,
3-carbomethoxyamino-7-(1H-2,1,4-benzothiadiazine)-sulfonic acid-2-methoxy-phenylester,
3-carbomethoxyamino-7-(1H-2,1,4-benzothiadiazine)-sulfonic acid-4-propoxy-phenylester,
3-carbomethoxyamino-7-(1H-2,1,4-benzothiadiazine)-sulfonic acid-4-isopropoxy-phenylester,
3-carbomethoxyamino-7-(1H-2,1,4-benzothiadiazine)-sulfonic acid-4-butoxy-phenylester,
3-carbomethoxyamino-7-(1H-2,1,4-benzothiadiazine)-sulfonic acid-4-isobutoxy-phenylester,
3-carbethoxyamino-7-(1H-2,1,4-benzothiadiazine)-sulfonic acid-phenylester,
3-carbopropoxyamino-7-(1H-2,1,4-benzothiadiazine)-sulfonic acid-phenylester,
3-isopropoxycarbonylamino-7-(1H-2,1,4-benzothiadiazine)-sulfonic acid-phenylester,
3-carbobutoxyamino-7-(1H-2,1,4-benzothiadiazine)-sulfonic acid-phenylester,
3-isobutoxycarbonylamino-7-(1H-2,1,4-benzothiadiazine)-sulfonic acid-phenylester,
3-carbo-b.butoxyamino-7-(1H-2,1,4-benzothiadiazine)-sulfonic acid-phenylester,
3-carbomethoxyamino-7-phenylsulfonyloxy-1H-2,1,4-benzothiadiazine,
3-carbomethoxyamino-7-(4-chloro-phenylsulfonyloxy)-1H-2,1,4-benzothiadiazine,
3-carbomethoxyamino-7-(3-chloro-phenylsulfonyloxy)-1H-2,1,4-benzothiadiazine,
3-carbomethoxyamino-7-(2-chloro-phenylsulfonyloxy)-1H-2,1,4-benzothiadiazine,
3-carbomethoxyamino-7-(2,5-dichloro-phenylsulfonyloxy)-1H-2,1,4-benzothiadiazine,
3-carbomethoxyamino-7-(3,4-dichloro-phenylsulfonyloxy)-1H-2,1,4-benzothiadiazine,
3-carbomethoxyamino-7-(3,5-dichloro-phenylsulfonyloxy)-1H-2,1,4-benzothiadiazine,
3-carbomethoxyamino-7-(4-bromo-phenylsulfonyloxy)-1H-2,1,4-benzothiadiazine,
3-carbomethoxyamino-7-(3-bromo-phenylsulfonyloxy)-1H-2,1,4-benzothiadiazine,
3-carbomethoxyamino-7-(2-bromo-phenylsulfonyloxy)-1H-2,1,4-benzothiadiazine,
3-carbomethoxyamino-7-(4-methyl-phenylsulfonyloxy)-1H-2,1,4-benzothiadiazine,
3-carbomethoxyamino-7-(3-methyl-phenylsulfonyloxy)-1H-2,1,4-benzothiadiazine,
3-carbomethoxyamino-7-(2-methyl-phenylsulfonyloxy)-1H-2,1,4-benzothiadiazine,
3-carbomethoxyamino-7-(4tert.butyl-phenylsulfonyloxy)-1H-2,1,4-benzothiadiazine,
3-carbomethoxyamino-7-(2-chloro-4-methyl-phenylsulfonyloxy)-1H-2,1,4-benzothiadiazine,
3-carbomethoxyamino-7-(2-chloro-6-methyl-phenylsulfonyloxy)-1H-2,1,4-benzothiadiazine,
3-carbomethoxyamino-7-(3-chloro-4-methyl-phenylsulfonyloxy)-1H-2,1,4-benzothiadiazine,
3-carbomethoxyamino-7-(3-chloro-6-methyl-phenylsulfonyloxy)-1H-2,1,4-benzothiadiazine,
3-carbomethoxyamino-7-(4-chloro-2-methyl-phenylsulfonyloxy)-1H-2,1,4-benzothiadiazine,
3-carbomethoxyamino-7-(4-chloro-3-methyl-phenylsulfonyloxy)-1H-2,1,4-benzothiadiazine,
3-carbomethoxyamino-7-(3-trifluoromethyl-phenylsulfonyloxy)-1H-2,1,4-benzothiadiazine,
3-carbomethoxyamino-7-(4-methoxy-phenylsulfonyloxy)-1H-2,1,4-benzothiadiazine,
3-carbomethoxyamino-7-(3-methoxy-phenylsulfonyloxy)-1H-2,1,4-benzothiadiazine,
3-carbomethoxyamino-7-(2-methoxy-phenylsulfonyloxy)-1H-2,1,4-benzothiadiazine,
3-carbomethoxyamino-7-(4-propoxy-phenylsulfonyloxy)-1H-2,1,4-benzothiadiazine,
3-carbomethoxyamino-7-(4-isopropoxy-phenylsulfonyloxy)-1H-2,1,4-benzothiadiazine,
3-carbomethoxyamino-7-(4-butoxy-phenylsulfonyloxy)-1H-2,1,4-benzothiadiazine,
3-carbomethoxyamino-7-(4-isobutoxy-phenylsulfonyloxy)-1H-2,1,4-benzothiadiazine, 3-carbethoxyamino-6-phenylsulfonyloxy-1H-2,1,4-benzothiadiazine,
3-carbopropoxyamino-6-phenylsulfonyloxy-1H-2,1,4-benzothiadiazine,
isopropoxycarbonylamino-6-phenylsulfonyloxy-1H-2,1,4-benzothiadiazine,
3-carbobutoxyamino-6-phenylsulfonyloxy-1H-2,1,4-benzothiadiazine,
3-isobutoxycarbonylamino-6-phenylsulfonyloxy-1H-2,1,4-benzothiadiazine,
3-carbo-t.-butoxyamino-6-phenylsulfonyloxy-1H-2,1,4-benzothiadiazine,
3-carbethoxyamino-6-(3-trifluoromethyl-phenylsulfonyloxy)-1H-2,1,4-benzothiadiazine,
3-isopropoxycarbonylamino-6-(3-trifluoromethyl-phenylsulfonyloxy)-1H-2,1,4-benzothiadiazine,
3-isobutoxycarbonylamino-6-(3-trifluoromethyl-phenylsulfonyloxy)-1H-2,1,4-benzothiadiazine.

The following compounds were prepared in this manner:
1-Acetyl-3-carbomethoxyamino-7-(1H-2,1,4-benzothiadiazine)-sulfonic acid-phenylester,
as well as the derivatives thereof which have been derived from the phenylester group according to the above enumeration;
1-propionyl-3-carbomethoxyamino-7-(1H-2,1,4-benzothiadiazine)-sulfonic acid-phenylester,
as well as the derivatives thereof which have been derived from the phenylester group according to the above enumeration;
1-benzoyl-3-carbomethoxyamino-7-(1H-2,1,4-benzothiadiazine)-sulfonic acid phenylester,
as well as the derivatives thereof wich have been derived from the phenylester group according to the above enumeration;
1-acetyl-3-carbethoxy (carbopropoxy, isopropoxycarbonyl, carbobutoxy, isobutoxycarbonyl)amino-7-(1H-2,1,4-benzothiadiazine)-sulfonic acid-phenylester;
1-acetyl-3-carbomethoxyamino-7-phenylsulfonyloxy-1H-2,1,4-benzothiadiazine,
as well as the derivatives thereof which have been derived from the phenylsulfonyloxy group according to the above enumeration; and in an analogous manner, the corresponding
1-benzoyl (propionyl)-3-carbethoxy (carbopropoxy, isopropoxycarbonyl, carbobutoxy, isobutoxycarbonyl)amino-7-phenylsulfonyloxy-1H-2,1,4-benzothiadiazine derivatives in accordance with the above enumeration.

The process described under (c) above is suitably carried out in a way that a solution of the corresponding 1H-2,1,4-benzothiadiazine derivative in a polar organic solvent is treated with a peroxo acid at a temperature in the range of from 10° to 30° C. As peroxo acids there are mentioned first of all, m-chloro-perbenzoic acid in a solvent, preferably chloroform or dioxan, or peracetic acid in glacial acetic acid. The S-oxide of the 1H-2,1,4-benzothiadiazine of the formula (1) is isolated, for example, by diluting the reaction mixture with water, in the case of the oxidation with peracetic acid, and by filtering off the precipitate formed with suction.

As starting compounds for the process described under (c) above there are mentioned in particular those 1H-2,1,4-benzothiadiazine derivatives which have been cited as starting compounds for the process described under (b).

The process for the preparation of the o-nitro-phenyl-thionocarbamoylcarbaminates used as intermediate products which have the formula (2), in which $R_1$, $R_2$, $R_3$ and X have the same meanings as in the formula (1) above, comprises reacting an o-nitro-aniline derivative of the formula (3)

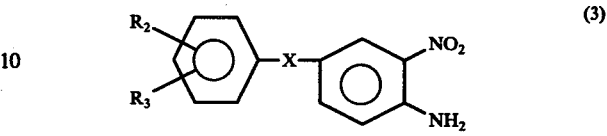

in which $R_2$, $R_3$ and X have the same meanings as in the formula (1) above, with an alkyl-isothiocyanato-formiate of the formula (4)

$$S = C = N - COOR_1 \quad (4)$$

in which $R_1$ is defined as in the formula (1) above.

In order to prepare the intermediate product of the formula (2), an o-nitraniline derivative of the formula (3) is reacted with an alkyl-isothiocyanato-formiate, depending on the reactivity of the starting materials, for one to several hours at a temperature in the range of from 20° to 120° C, in which process the alkyl-isothiocyanato-formiate is suitably used in an excess amount, so that it serves also as a solvent. The reaction products are isolated by evaporating the excess alkyl-isothiocyanato-formiate, and the residue is extracted with an inert solvent, as those mentioned above in the process described under (b).

As o-nitraniline derivatives in accordance with the formula (3) there may be mentioned, for example, 2-nitro-4-phenyloxysulfonyl-aniline,
2-nitro-4-(4-chloro-phenoxysulfonyl)-aniline,
2-nitro-4-(3-chloro-phenoxysulfonyl)-aniline,
2-nitro-4-(2-chloro-phenoxysulfonyl)-aniline,
2-nitro-4-(2,5-dichloro-phenoxysulfonyl)-aniline,
2-nitro-4-(3,5-dichloro-phenoxysulfonyl)-aniline,
2-nitro-4-(4-bromo-phenoxysulfonyl)-aniline,
2-nitro-4-(3-bromo-phenoxysulfonyl)-aniline,
2-nitro-4-(2-bromo-phenoxysulfonyl)-aniline,
2-nitro-4-(4-methyl-phenoxysulfonyl)-aniline,
2-nitro-4-(3-methyl-phenoxysulfonyl)-aniline,
2-nitro-4-(2-methyl-phenoxysulfonyl)-aniline,
2-nitro-4-(4-t.butyl-phenoxysulfonyl)-aniline,
2-nitro-4-(2,4-dimethyl-phenoxysulfonyl)-aniline,
2-nitro-4-(2-chloro-4-methyl-phenoxysulfonyl)-aniline,
2-nitro-4-(2-chloro-6-methyl-phenoxysulfonyl)-aniline,
2-nitro-4-(3-chloro-4-methyl-phenoxysulfonyl)-aniline,
2-nitro-4-(3-chloro-6-methyl-phenoxysulfonyl)-aniline,
2-nitro-4-(4-chloro-2-methyl-phenoxysulfonyl)-aniline,
2-nitro-4-(4-chloro-3-methyl-phenoxysulfonyl)-aniline,
2-nitro-4-(3-trifluoromethyl-phenoxysulfonyl)-aniline,
2-nitro-4-(4-methoxy-phenoxysulfonyl)-aniline,
2-nitro-4-(3-methoxy-phenoxysulfonyl)-aniline,
2-nitro-4-(2-methoxy-phenoxysulfonyl)-aniline,
2-nitro-4-(4-propoxy-phenoxysulfonyl)-aniline,
2-nitro-4-(4-isopropoxy-phenoxysulfonyl)-aniline,
2-nitro-4-(4-butoxy-phenoxysulfonyl)-aniline,
2-nitro-4-(4-isobutoxy-phenoxysulfonyl)-aniline,
2-nitro-4-phenylsulfonyloxy-aniline,
2-nitro-4-(4-chloro-phenylsulfonyloxy)-aniline,
2-nitro-4-(3-chloro-phenylsulfonyloxy)-aniline,
2-nitro-4-(2-chloro-phenylsulfonyloxy)-aniline,
2-nitro-4-(2,5-dichloro-phenylsulfonyloxy)-aniline, 2-nitro-4-(3,4-dichloro-phenylsulfonyloxy)-aniline,
2-nitro-4-(3,5-dichloro-phenylsulfonyloxy)-aniline,
2-nitro-4-(4-bromo-phenylsulfonyloxy)-aniline,
2-nitro-4-(3-bromo-phenylsulfonyl)-aniline,
2-nitro-4-(2-bromo-phenylsulfonyloxy)-aniline,
2-nitro-4-(4-methyl-phenylsulfonyloxy)-aniline,
2-nitro-4-(3-methyl-phenylsulfonyloxy)-aniline,
2-nitro-4-(2-methyl-phenylsulfonyloxy)-aniline,
2-nitro-4-(4-tert.butyl-phenylsulfonyloxy)-aniline,
2-nitro-4-(2-chloro-4-methyl-phenylsulfonyloxy)-aniline,
2-nitro-4-(2-chloro-6-methyl-phenylsulfonyloxy)-aniline
2-nitro-4-(3 -chloro-3-methyl-phenylsulfonyloxy)-aniline,
2-nitro-4-(3-chloro-6-methyl-pyhenylsulfonyloxy)-aniline,
2-nitro-4-(4-chloro-2-methyl-phenylsulfonyloxy)-aniline
2-nitro-4-(4-chloro-3-methyl-phenylsulfonyloxy)-aniline,
2-nitro-4-(3-trifluorometyl-phenylsulfonyloxy)-aniline,
2-nitro-4-(4-methoxy-phenysulfonyloxy)-aniline,
2-nitro-4-(3-methoxy-phenylsulfonyloxy)-aniline,
2-nitro-4-(2-methoxy-phenylsulfonyloxy)-aniline,
2-nitro-4-(4-propoxy-phenylsulfonyloxy)-aniline,
2-nitro-4-(4-isopropoxy-phenylsulfonyloxy)-aniline,
2-nitro-4-(4-butoxy-phenylsulfonyloxy)-aniline,
2-nitro-4-(4-isobutoxy-phenylsulfonyloxy)-aniline.

As alkyl-isothiocyanato-formiates of the formula (4) there may be mentioned methyl-, ethyl-, propyl-, isopropyl-, butyl-, isobutyl-, and tertiary butyl-isothiocyanato-formiate.

The o-nitraniline derivatives of the formula (3) which are required for the preparation of the o-nitrophenyl-thionocarbamoyl-carbaminates of the formula (2) used as intermediate products are obtained in their turn in the case, where X represents the group —O—SO$_2$, by reacting the corresponding chloro-nitro compounds of the following formula (4a), in which R$_2$ and R$_3$ have the same meanings as in formula (1) above, with ammonia in a suitable solvent, such as dioxan or methanol, at an elevated temperature and an increased pressure. The chloro-nitro compounds of the formula (5) in their turn are obtained by reacting 3-nitro-4-chloro-benzene-sulfonic acid-chloride (6) with a phenol of the following formula (7), in which R$_2$ and R$_3$ are defined as in the formula (1) above, in an inert solvent in the presence of a base, such as triethylamine.

In the case where X represents the group —SO$_2$—O, the corresponding o-nitraniline derivatives of the formula (3) are obtained by reacting 3-nitro-4-aminophenol (8) with a benzene-sulfonic acid-chloride of the formula (9), in which R$_2$ and R$_3$ have the same meanings as in the formula (1), in an inert solvent in the presence of a base, such as triethylamine.

The development of the reactions is illustrated by the following scheme:

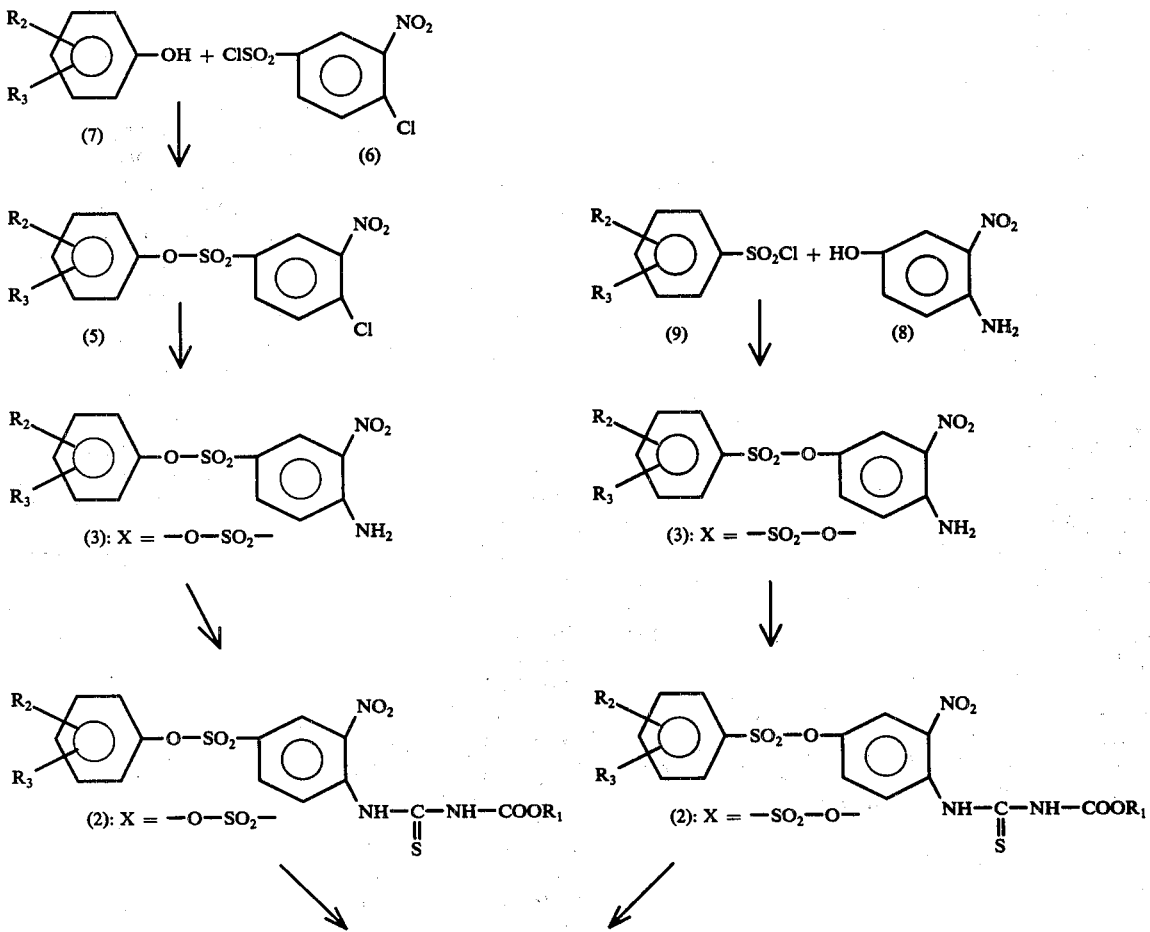

-continued

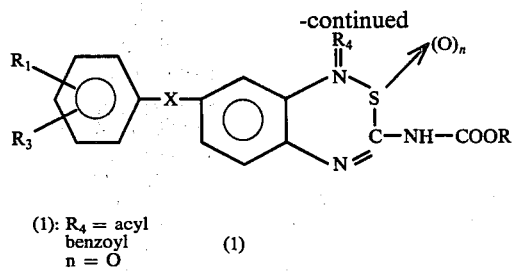

(1): $R_4$ = acyl
benzoyl (1)
n = O (1): $R_4$ = H
n = o

The 1H-2,1,4-benzothiadizine derivatives of the formula (1) and the o-nitrophenyl-thionocarbamoyl-carbaminates of the formula (2) are anthelmintically active. Moreover, the 1H-2,1,4-benzothiadiazine derivatives of the formula (1) are valuable intermediate products for the preparation of further benzimidazole derivatives having an anthelmintic effect.

The novel compounds of the formula (1) are especially active against a great number of helminths, for example, Haemonchus, Trichostrongylus, Ostertagia, Strongyloides, Cooperia, Chaberta, Oesophagostomum, Hyostrongylus, Ankylostoma, Askaris, and Heterakis. Particularly marked is the activity against gastro-intestinal Strongylides, which, above all, infest ruminants. Besides, they act against liver flukes.

The active substances are administered orally or subcutaneously in conjunction with suitable pharmaceutical solvents and/or carriers the one or the other form of administration being preferred depending on the respective circumstances.

The active substances of the formula (1) are administered, depending on the case, in a dosage of from 0.5 to 50 mg per kg of body weight for a period of from 1 to 14 days.

For an oral administration there are suitable tablets, dragees, capsules, powders, granules, or pastes which contain the active substances in conjunction with common auxiliary or carrier substances, such as starch, cellulose powder, talcum, magnesum stearate, sugar, gelatin, calcium carbonate, finely divided silicic acid, carboxymetyl cellulose, or similar substances.

The following Examples serve to illustrate the invention.

EXAMPLES 1. 10.0 Grams of 2-nitro-4-phenoxysulfonyl-phenyl-thionocarbamoyl-methyl-carbaminate were dissoled with the exclusion of air in 280 ml of 0.5N sodium hydroxide solution, and at a temperature of from 20° to 25° C a solution of 14 g of sodium dithionite in 140 ml of water was slowly added, while stirring. After 30 minutes the mixture was acidified with diluted hydrochloric acid, and the separated precipitate of the 3-carbomethoxyamino-7-(1H-2,1,4-benzothiadiazine)-sulfonic acid-phenylester was filtered off.

After washing with water and drying over potassium hydroxide in vacuo, 7.2 g of 3-carbomethoxyamino-7-(1H-2,1,4-benzothiadiazine)-sulfonic acid-phenylester were obtained, which had a sintering point of 130° C.

The 2-nitro-4-phenyl-sulfonylphenyl-thionocarbamoyl-methylcarbaminate, required for the reaction was prepared by heating 29.4 g of 2-nitro-4-phenoxysulfonyl-aniline in 30 ml of methyl-isothiocyanato-formiate for 1 hour to 100° C, while stirring. After cooling to 30° C, a total of 200 ml of diisopropylether was slowly added to the mixture, which was then cooled in an ice bath, and the precipitated 2-nitro-4-phenoxysulfonyl-phenylthionocarbamoyl-methylcarbaminate was filtered off. It was sufficiently pure for further processing. The yield was 25 g, melting point 137° C.

In order to prepare the 2-nitro-4-phenoxysulfonyl-aniline, 54 g of 3-nitro-4-chloro-benzene-sulfonic acid-phenylester in 500 ml of dioxan were maintained at 5 atmospheres gage of gaseous ammonia for 5 hours at 50° C, and the solvent was subsequently eliminated in vacuo. The residue was mixed with 200 ml of a toluene of equal parts of methanol and water, in which process a solid precipitate was formed after a short time, which was filtered off. After a recrystallization from methanol and from benzene, 28 g of 2-nitro-4-phenoxysulfonyl-aniline were obtained, which had a melting point of 104° C.

3-Nitro-4-Chloro-benzene-sulfonic acid-phenylester was obtained by mixing 51 g of 3-nitro-4-chloro-benzene-sulfonic acid-chloride with 18.8 g of phenol in 120 ml of acetone, and by adding 28 ml of triethylamine dropwise, while cooling, at a temperature not exceeding 10° C. The mixture was continued to be stirred for several hours at room temperature, and then water was added, in which process an oil was separated which was extracted with ether. After recrystallization of the residue from methanol, 54 g of 3-nitro-4-chloro-benzene-sulfonic acid-phenylester were obtained, which had a melting point of 71° C.

In an analogous manner, the following compounds were prepared using starting materials which had been modified accordingly:

2 From 3-nitro-4-chloro-benzene-sulfonic acid-4-chloro-phenylester via 2-nitro-4-(4-chloro-phenoxysulfonyl)-aniline and 2-nitro-4-(4-chloro-phenoxysulfonyl)-phenyl-thionocarbamoyl-methylcarbaminate, 3-carbomethoxyamino-7-(1H-2,1,4-benzothiadiazine)-sulfonic acid-4-chloro-phenylester;

3. from 3-nitro-4-chloro-benzene-sulfonic acid-3-chloro-phenylester via 2-nitro-4-(3-chloro-phenoxysulfonyl)-aniline and 2-nitro-4-(3-chloro-phenoxysulfonyl)-phenyl-thionocarbamoyl-methylcarbaminate, 3-carbomethoxyamino-7-(1H-2,1,4-benzothiadiazine)-sulfonic acid-3-chloro-phenylester;

4. from 3-nitro-4-chloro-benzene-sulfonic acid-3,5-dichloro-phenylester via 2-nitro-4-(3,5-dichloro-phenoxysulfonyl)-aniline and 2-nitro-4-(3,5-dichloro-phenoxysulfonyl)-phenyl-thionocarbamoylmethylcarbaminate, 3-carbomethoxyamino-7-(1H-2,1,4-benzothiadiazine)-sulfonic acid-3,5-dichloro-phenylester;

5. from 3-nitro-4-chloro-benzene-sulfonic acid-3-bromo-phenylester via 2-nitro-4-(3-bromo-phenoxysulfonyl)-aniline and 2-nitro-4-(3-bromo-phenoxysulfonyl)-phenyl-thionocarbamoyl-methylcarbaminate, 3-carbomethoxyamino-7-(1H-2,1,4-benzothiadiazine)-sulfonic acid-3-bromo-phenylester;

6. from 3-nitro-4-chloro-benzene-sulfonic acid-4-methyl-phenylester via 2-nitro-4-(4-methyl-phenoxysulfonyl)-aniline and 2-nitro-4-(4-methyl-phenoxysulfonyl)-phenyl-thionocarbamoyl-methylcarbaminate, 3-carbomethoxyamino-7-(1H-2,1,4-benzothiadiazine)-sulfonic acid-4-methyl-phenylester;

7. from 3-nitro-4-chloro-benzene-sulfonic acid-3-methyl-phenylester via 2-nitro-4-(3-methyl-phenoxysulfonyl)-aniline and 2-nitro-4-(3-methyl-phenoxysulfonyl)-phenyl-thionocarbamoyl-methylcarbaminate, 3-carbomethoxyamino-7-(1H-2,1,4-benzothiadiazine)-sulfonic acid-3-methyl-phenylester;

8. from 3-nitro-4-chloro-benzene-sulfonic acid-4-methoxy-phenylester via 2-nitro-4-(4-methoxy-phenoxysulfonyl)-aniline and 2-nitro-4-(4-methoxy-phenoxysulfonyl)-phenyl-thionocarbamoyl-methylcarbaminate, 3-carbomethoxyamino-7-(1H-2,1,4-benzothiadiazine)-sulfonic acid-4-methoxy-phenylester;

9. from 3-nitro-4-chloro-benzene-sulfonic acid-3-methoxy-phenylester via 2-nitro-4-(3-methoxy-phenoxysulfonyl)-aniline and 2-nitro-4-(3-methoxy-phenoxysulfonyl)-phenyl-thionocarbamoyl-methylcarbaminate, 3-carbomethoxyamino-7-(1H-2,1,4-benzothiadiazine)-sulfonic acid-3-methoxy-phenylester;

10. from 3-nitro-4-chloro-benzene-sulfonic acid-3-ethoxy-phenylester via 2-nitro-4-(3-ethoxy-phenoxysulfonyl)-aniline and 2-nitro-4-(3-ethoxy-phenoxysulfonyl)-phenyl-thionocarbamoyl-methylcarbaminate, 3-carbomethoxyamino-7-(1H-2,1,4-benzothiadiazine)-sulfonic acid-3-ethoxy-phenylester;

11. from 3-nitro-4-chloro-benzene-sulfonic acid-3-cyano-phenylester via 2-nitro-4-(3-cyano-phenoxysulfonyl)-aniline and 2-nitro-4-(3-cyano-phenoxysulfonyl)-phenyl-thionocarbamoyl-methylcarbaminate, 3-carbomethoxyamino-7-(1H-2,1,4-benzothiadiazine)-sulfonic acid-3-cyano-phenylester;

12. from 3nitro-4-chloro-benzene-sulfonic acid-3-trifluoromethyl-phenylester having a melting point of 65° C via 2-nitro-4-(3-trifluoromethyl-phenoxysulfonyl)-aniline (m.p. of 131° C) and 2-nitro-4-(3-trifluoromethyl-phenoxysulfonyl)-phenyl-thionocarbamoyl-methylcarbaminate (m.p. of 157° C), 3-carbomethoxyamino-7-(1H-2,1,4-benzothiadiazine)-sulfonic acid-3-trifluoromethyl-phenylester having a melting point of 158° C (decomp.)

13. 10.0 Grams of 2-nitro-4-phenylsulfonyloxy-phenyl-thionocarbamoyl-methylcarbaminate, were dissolved with the exclusion of air in 280ml of 0.5N sodium hydroxide solution, and at a temperature in the range of from 20 to 25° C, a solution of 14 g of sodium dithionite in 140 ml of water was slowly added, while stirring. After 30 minutes the mixture was acidified with diluted hydrochloric acid, and the separated precipitate of the 3-carbomethoxyamino-7-phenylsulfonyloxy-1H-2,1,4-benzothiadiazine was filtered off with suction. After washing with water and drying over KOH in vacuo the yield was 5.5 g having a melting point of 145° C.

The 2-nitro-4-phenylsulfonyloxy-phenyl-thioncarbamoyl-methylcarbaminate required for the reaction was prepared by heating 29.4 g of 2-nitro-4-phenyl-sulfonyloxy-aniline in 30 ml of methyl-isothiocyanato-formiate for 1 hour at 100° C, while stirring. After cooling to 30° C, a total of 200 ml of diisopropylether was slowly added to the mixture, which was then cooled in an ice bath, and the precipitated 2-nitro-4-phenylsulfonyloxy-phenyl-thionocarbamoyl-methylcarbaminate was filtered off with suction. The product was recrystallized from a mixture of methylglycol and methanol, and 30 g of the above-mentioned substance were obtained, which had a melting point of 134° C.

In order to prepare 2-nitro-4-phenylsulfonyloxy-aniline, 15.4 g of 3-nitro-4-amino-phenol in 100 ml of acetone were mixed with 14 ml of triethylamine, and 17.6 g of benzane-sulfonic acid-chloride dissolved in 30 ml of acetone were added dropwise, while stirring, at an internal temperature not exceeding 20° C in an ice bath. The mixture was continued to be stirred for another 3 hours at room temperature, the triethylamine-hydrochloride was filtered off, and the filtrate was evaporated to dryness. The residue was then stirred with 50 ml of methanol and was filtered. After washing with methanol and drying, 18.2 g of 2-nitro-phenylsulfonyloxy-aniline were obtained, which has a melting point of 140° C.

In an analogous manner, the following compounds were prepared, while using starting materials which had been modified accordingly:

14. From 2-nitro-4-(4-chloro-phenylsulfonyloxy)-aniline via 2-nitro-4(4-chloro-phenylsulfonyloxy)-phenyl-thionocarbamoyl-methylcarbaminate, 3-carbomethoxyamino-7-(4-chloro-phenylsulfonyloxy)-1H-2,1,4-benzothiadiazine;

15. from 2-nitro-4-(3-chloro-phenylsulfonyloxy)-aniline via 2-nitro-4-(3-chloro-phenylsulfonyloxy)-phenyl-thionocarbamoyl-methylcarbaminate, 3-carbomethoxyamino-7-(3-chloro-phenylsulfonyloxy)-1H-2,1,4-benzothiadiazine;

16. from 2-nitro-4-(3,4-dichloro-phenylsulfonyloxy)-aniline via 2-nitro-4(3,4-dichloro-phenylsulfonyloxy)-phenyl-thionocarbamoyl-methylcarbaminate, 3-carbomethoxyamino-7-(3,4-dichloro-phenylsulfonyloxy)-1H-2,1,4-benzothiadiazine;

17. from 2-nitro-4-(3,5-dichloro-phenylsulfonyloxy)-aniline via 2-nitro-4-(3,5-dichloro-phenylsulfonyloxy)-phenyl-thionocarbamoyl-methylcarbaminate, 3-carbomethoxyamino-7-(3,5-dichloro-phenylsulfonyloxy)-1H-2,1,4-benzothiadiazine;

18. from 2-nitro-4-(3-bromo-phenylsulfonyloxy)-aniline via 2-nitro-4-(3-bromo-phenylsulfonyloxy)-phenyl-thionocarbamoyl-methylcarbaminate, 3-carbomethoxyamino-7-(3-bromo-phenylsulfonyloxy)-1H-2,1,4-benzothiadiazine;

19. from 2-nitro-4-(4-methyl-phenylsulfonyloxy)-aniline via 2-nitro-4-(4-methyl-phenylsulfonyloxy)-phenyl-thionocarbamoyl-methylcarbaminate, 3-carbomethoxyamino-7-(4-methyl-phenylsulfonyloxy)-1H-2,1,4-benzothiadiazine;

20. from 2-nitro-4-(3-methyl-phenylsulfonyloxy)-aniline via 2-nitro-4-(3-methyl-phenylsulfonyloxy)-phenyl-thionocarbamoyl-methylcarbaminate, 3-carbomethoxyamino-7-(3-methyl-phenylsulfonyloxy)-1H-2,1,4-benzothiadiazine;

21. from 2-nitro-4-(3-trifluoromethyl-phenylsulfonyloxy)-aniline (m.p. of 132° C) via 2-nitro-4-(3-trifluoromethyl-phenylsulfonyloxy)-phenyl-thionocarbamoyl-methylcarbaminate (m.p. of 126° C), 3-carbomethoxyamino-7-(3-triifluoromethyl-phenylsulonyloxy)-1H-2,1,4-benzothiadiazine having a sintering point of 72° C.

22. from 2-nitro-4-(3-trifluoromethyl-phenylsulfonyloxy)-aniline via 2-nitro-4-(3-trifluoromethylphenylsulfonyloxy)-phenyl-thionocarbamoyl-ethylcarbaminate, 3-carboethoxyamino-7-(3-trifluoromethylphenylsulfonyloxy)-1H-2,1,4-benzothiadiazine;

23. from 2-nitro-4-(3-trifluoromethyl-phenylsulfonyloxy)-aniline via 2-nitro-4-(3-trifluoromethylphenylsulfonyloxyy)-phenyl-thionocarbamoyl-isopropylcarbaminate, 3-isopropoxycarbonylamino-7-(3- trifluorromethyl-phenylsulfonyloxy)1H-2,1,4-benzothiadiazine;

24. froum 2-nitro-4-(3-trifluoromethyl-phenylsulfonyloxy)-aniline via 2-nitro-4-(3-trifluoromethyl-phenylsulfonyloxy)-phenyl-thionocarbamoyl-isobutoxycarbaminate, 3-isobutoxycarbonylamino-7-(3-trifluoromethyl-phenylsulfonyloxy)1H-2,1,4-benzothiadiazine.

(Process b)

25. Milliliter of acetyl chloride was added dropwise, while stirring and cooling with an ice mixture, to a solution of 1.36 g of 3-carbomethoxyamino-7-(3-trifluoromethyl-phenylsulfonyloxy)-1H-2,1,4benzothiadiazine in 20 ml of pyridine. After the mixture had been stirred for 2 hours at 0° C, 1 ml of acetyl chloride was added once more. After another hour of stirring at 0° C, the reaction mixture was diluted with water. It was then shaken with ethyl acetate, and the extract was washed with saturated sodium chloride solution. After evaporation of the solvent, the residue was isolated by trituration with methanol and filtration. 1-Acetyl-3-carbomethoxy-amino-7-(3-trifluoromethyl-phenylsulfonyloxy)-1H-2,1,4-benzothiadiazine was obtained in a yield of 1.0 g.

(Process c)

26. A solution of 240 mg of m-chloroperbenzoic acid in 10 ml of dioxan was introduced, while stirring, into a solution of 0.54 g of 3-carbomethoxyamino-7-(3-trifluoromethyl-phenylsulfonyloxy)-1H-2,1,4-benzothiadiazine in 50 ml of dioxan. The mixture was stirred for 15 minutes, then it was diluted with 100 ml of water, neutralized with sodium carbonate solution, and subsequently the whole was shaken with ethyl acetate. After washing out the ester extract with sodium chloride solution, the ester solution was strongly concentrated, and the separated 3-carbomethoxyamino-7-(3-trifluoromethyl-phenylsulfonyloxy)-1H-2,1,4-benzothiadiazine-S-oxide was isolated by way of filtration. The yield was 120 mg.

(Process b)

27. 1 Milliliter of benzoyl chloride was added dropwise, while stirring and cooling with an ice mixture, to a solution of 1.4 g of 3-carbomethoxyamino-7-(3-trifluoromethyl-phenylsulfonyloxy)-1H-2,1,4-benzothiadiazine-S-oxide in 20 ml of pyridine. After the mixture has been stirred for 2 hours at 0° C, 1 ml of benzoyl chloride was added once more. After another hour of stirring at 0° C, the reaction mixture was diluted with water. It was then shaken with ethyl acetate, and the extract was washed with saturated sodium chloride solution. After evaporation of the solvent, the residue was isolated by trituration with methanol and filtration. 1-Benzoyl-3-carbomethoxyamino-7-(3-trifluoromethyl-phenylsulfonyloxy)-1H-2,1,4-benzothiadiazine-S-oxide was obtained in a yield of 1.1 g.

We claim:

1. A compound of the formula

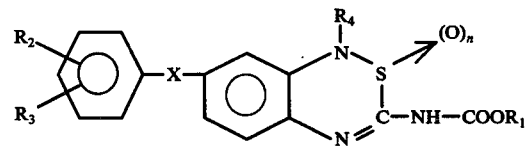

wherein $R_1$ is alkyl having 1 to 4 carbon atoms; $R_2$ and $R_3$ are the same or different and are each hydrogen, alkoxy having 1 to 4 carbon atoms, halogen, trifluoromethyl, alkyl having 1 to 4 carbon atoms, or cyano; $R_4$ is hydrogen, alkanoyl having 2 to 4 carbon atoms, or benzoyl; $n$ is 0 or 1: and X is —O—SO$_2$—or —SO$_2$—O—.

2. A compound as in claim 1 wherein $R_1$ is methyl; $R_2$ is hydrogen or trifluoromethyl; $R_3$ and $R_4$ are hydrogen; and $n$ is O.

3. A pharmaceutical composition for combatting helminths, which composition comprises and anthelmintically-effective amount of a compound as in claim 1 in combination with a pharmaceutical carrier.

4. The method of combatting helminths in an organism infested therewith, which method comprises administering to said organism an anthelmintically-effective amount of a compound as in claim 1.

5. 3-Carbomethoxyamino-7-(1H-2,1,4-benzothiadiazine)sulfonic acid-phenylester.

6. 3-Carbomethoxyamino-7-(1H-2,1,4-benzothiadiazine)sulfonic acid-3-trifluoromethyl-phenylester.

7. 3-Carbomethoxyamino-7-(3-trifluoromethyl-phenylsulfonyloxy)-1H-2,1,4-benzothiadiazine.

* * * * *